United States Patent
Takeda et al.

(10) Patent No.: US 7,313,426 B2
(45) Date of Patent: Dec. 25, 2007

(54) APPARATUS FOR DETERMINING CONCENTRATIONS OF LIGHT ABSORBING SUBSTANCES IN BLOOD

(75) Inventors: Sunao Takeda, Tokyo (JP); Naoki Kobayashi, Tokyo (JP); Hiroshi Kubota, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 283 days.

(21) Appl. No.: 11/090,239

(22) Filed: Mar. 28, 2005

(65) Prior Publication Data

US 2005/0250997 A1 Nov. 10, 2005

(30) Foreign Application Priority Data

Mar. 29, 2004 (JP) ............ P2004-094581

(51) Int. Cl.
*A61B 5/00* (2006.01)
(52) U.S. Cl. ............... 600/322; 600/330
(58) Field of Classification Search ........... 600/300, 600/310, 322, 323
See application file for complete search history.

(56) References Cited

U.S. PATENT DOCUMENTS

| | | | |
|---|---|---|---|
| 4,700,708 A | * | 10/1987 | New et al. ............ 600/331 |
| 4,759,369 A | * | 7/1988 | Taylor ............... 600/323 |
| 5,590,652 A | | 1/1997 | Inai |
| 5,746,697 A | | 5/1998 | Swedlow et al. |
| 6,005,658 A | | 12/1999 | Kaluza et al. |

FOREIGN PATENT DOCUMENTS

| | | |
|---|---|---|
| JP | 6-63032 A | 3/1994 |
| JP | 10-314150 A | 12/1998 |
| JP | 2000-504599 A | 4/2000 |
| JP | 2003-240716 A | 8/2003 |

OTHER PUBLICATIONS

Clinical Engineering vol. 7, No. 2, pp. 102-110 (1996).
Handbook of Medical and Biological Engineering Equipments (revised version) pp. 130-132 (1996).

* cited by examiner

*Primary Examiner*—Eric Winakur
*Assistant Examiner*—Etsub D Berhanu
(74) *Attorney, Agent, or Firm*—Sughrue Mion Pllc.

(57) ABSTRACT

In an apparatus for determining a concentration of a light absorbing substance in blood, a plurality of photo emitters are adapted to emit light beams having different wavelengths toward a living tissue including a blood vessel. A photo receiver is adapted to receive the light beams which have been transmitted through or reflected from the living tissue. A driver inputs driving currents for causing the respective photo emitters to emit the light beams. An optimizer obtains values of AC components of the light beams received by the photo receiver, and adjusts values of the driving currents such that the values of the AC components fall within a predetermined range.

2 Claims, 4 Drawing Sheets

APPARATUS FOR DETERMINING CONCENTRATIONS OF LIGHT ABSORBING SUBSTANCES IN BLOOD

BACKGROUND OF THE INVENTION

The present invention relates to an improvement of an apparatus which irradiates light on living tissue of a patient, and detects light transmitted through or reflected by the living tissue, thereby determining concentrations of light absorbing substances in blood.

Pulsating components of light transmitted through or reflected by living tissue include information on light absorption characteristics of light absorbing substances in blood.

Accordingly, by measuring pulsating components of light transmitted through or reflected by living tissue with use of a plurality of wavelengths, ratios between concentrations of a plurality of light absorbing substances in blood can be measured.

This basic principle has a wide range of applications, and is given the generic name of pulse photometry. One application of the principle is a pulse oximeter which determines arterial oxygen saturation continuously in a noninvasive manner.

Since a change in the condition of a patient requires an immediate response, an important consideration for such a pulse oximeter is use in a continuous monitoring mode. Also, such a pulse oximeter is desirably portable so as to be carried from one room to another without requiring insertion in a power receptacle. Power consumption is a problem for such a portable type pulse oximeter, and reduction in (conservation of) power consumption has been desired.

The same problem described above applies to other apparatus for determining concentrations of light absorbing substances in blood, such as hemoglobin concentration, dye concentration, bilirubin concentration, and blood glucose level.

A configuration of a conventional pulse oximeter and light-emitting timings of LEDs serving as a light source will be described by reference to FIGS. 5A and 5B. Such a configuration is disclosed in "Clinical Engineering Vol. 7, No. 2 (1996) pp 102-110" and "Handbook of Medical and Biological Engineering Equipments (revised version; 1996), pp 130-132", for example.

As shown in FIG. 5A, a pulse oximeter comprises a probe P attached to a portion (e.g., a finger) of a patient, and a main body H for processing a signal output from the probe.

The probe includes an LED section 1 serving as a light-emitter which comprises a first LED 1a for emitting red light of a first wavelength and a second LED 1b for emitting infrared light of a second wavelength; and a light-receiver constituted of a photodiode 3 for receiving light transmitted through or reflected by tissue of the patient to whose finger, or the like, the probe is attached.

The first wavelength of red light is in the vicinity of 680 nm and the second wavelength of infrared radiation is in the vicinity of 940 nm are generally used, and the LEDs 1a, 1b in the LED section 1 are alternately caused to illuminate.

The main body H of the pulse oximeter includes a current-voltage converter 4, a demodulator 5, a pulsation ratio detector 7, an attenuation ratio calculator 8, an oxygen saturation calculator 9, an LED driving current calculator 10, and an LED driver 2.

In the configuration shown in FIG. 5A, intensity of light, which has been emitted from the LED section 1, passed through tissue such as a finger, and reached the photodiode 3, is converted into current by the photodiode 3.

The intensity of light which has been converted into current is converted into voltage by the current-voltage converter 4 in the main body H, and separated into a transmitted-light signal of red light and that of infrared light, respectively, by way of the demodulator 5.

Each of the thus-separated transmitted-light signals indicates a waveform in which a pulse wave component (AC component) is superimposed on a DC component (DC component).

The respective transmitted-light signals are separated into the DC component and the AC component at the pulsation ratio detector 7, whereby a pulsation ratio (AC component/DC component) is calculated.

For calculation of oxygen saturation, an attenuation change $\Delta A$ must be obtained, which can be approximated by a pulsation ratio. Accordingly, pulsation ratios of the respective red light and infrared light are extracted as attenuation changes ($\Delta A1$, $\Delta A2$) from the pulsation ratio detector 7. The thus-extracted pulsation ratios are processed by the attenuation ratio calculator 8 to calculate a ratio thereof ($\Phi = \Delta A1 / \Delta A2$), and converted into oxygen saturation in the oxygen saturation calculator 9. A pulse rate can also be obtained simultaneously.

Next, light-emitting timings of the wavelengths 1 and 2 emitted alternately from the first LED 1a and the second LED 1b will be described by reference to FIG. 5B.

In FIG. 5B, "a" indicates a light-emitting timing of the first LED 1a and "b" indicates the same of the second LED 1b; and "a" and "b" are controlled by the LED driver 2 so as to alternately illuminate in a frequency range of hundreds of Hz to some KHz. "c" is an output from the photodiode 3 in response to received light, and indicates a value of intensity of transmitted light of the first wavelength and that of the second wavelength which have been converted into electric signals. "a1" indicates intensity of the transmitted light of the first wavelength received by the photodiode 3, and "a2" indicates the same of the second wavelength.

In a conventional control for reducing power consumption, attention has been focused on the DC component, and drive current of the LED section 1 has been controlled such that the LED driving current calculator 10 calculates an optimum LED driving current in accordance with the DC component of the transmitted light, whereby the optimum LED driving current is supplied to the LED section 1 by the LED driver 2.

Control modes of drive current include decreasing amplitude of a current pulse, or narrowing a pulse width of a current pulse. Examples of such control modes are shown in FIG. 3. The upper diagram shows an example where a width of a current pulse in a single period is narrowed, and the lower diagram shows an example where an amplitude of a current pulse is decreased.

In the conventional pulse oximeter, in order to control the LED driving current for the purpose of power-saving, attention is focused on the DC component. When the DC component is large, an amount of transmitted light received by the photodiode 3 is determined to be large, and the LED driving current is reduced so as to reduce an amount of light emitted from the LED section 1.

However, in a case of a patient whose pulse wave is small, the AC component is small even when the DC component is large. Accordingly, when the amount of light emitted from the LED section 1 is reduced, detection of the AC component which can maintain measurement accuracy as a pulse oximeter becomes difficult.

Therefore, when the LED driving current is controlled by reference solely to a value of the DC component, measurement of an arterial oxygen saturation (SpO2) can be performed in some cases but not in other cases in accordance with the status (magnitude of an AC component) of a patient.

In order to avoid the problem, there must be supplied an LED driving current that consistently maintains an amount of light emitted from the LED, by which the oxygen saturation (SpO2) of a patient who is assumed to have a small pulse wave (i.e., AC component thereof is small) can be measured.

In this case, there arises a problem that, since an LED current larger than required is supplied to a patient having a large AC component, sufficient control for power-saving cannot be achieved.

This situation will be described by reference to FIG. 4, which is a graph where the horizontal axis represents a DC component of transmitted light to be input into the current-voltage converter 4, and the vertical axis represents a pulsation ratio, which is a ratio between the AC component and the DC component of the transmitted light. The thick solid line indicates a boundary at which the AC component is 100 (pA), (this value is set to a magnitude with which a sufficient signal to noise ratio can be ensured in relation to noise of the measurement system, and varies in some cases depending on the type of a pulse oximeter; and the value is not limited to 100 (pA)) which is a limit value where an arterial oxygen saturation (SpO2) can be measured by a pulse oximeter.

A pulse oximeter has a characteristic such that when the AC component falls lower than 100 (pA), measurement of the AC component becomes impossible. More specifically, the right side including the boundary indicates a region where the arterial oxygen saturation (SpO2) can be calculated, whereas the left side indicates a region where the arterial oxygen saturation (SpO2) cannot be measured.

Here, on the assumption that a DC component of transmitted light obtained is 100 (nA) and a pulsation ratio is 1 (%) when an electric current of Ao (mA) is supplied to the LED section 1, the pulse wave comes to a point "a" in FIG. 4.

Next, while attention is focused on the DC component, when the LED driving current section 1 is caused to decrease to an appropriate value A (mA) so as to decrease the DC component from the present 100 (nA) to 10 (nA). At this time, on the assumption that the pulsation ratio does not change during a short period of time, the point "a" moves horizontally to the point "b" in parallel with the axis. In this case, as understood from FIG. 4, measurement of the arterial oxygen saturation (SpO2) remains to be possible even when the LED current is decreased from Ao (mA) to A (mA).

However, under such a control where attention is focused on the DC component, even on the assumption that an AC component of light transmitted through a patient is always small and, upon supply of electric current of Ao (mA) to the LED section 1, a DC component of 100 (nA) is obtained, when the AC component is assumed to be 0.5 (nA), the pulsation ratio becomes 0.5 (%), which is plotted as "c" in FIG. 4.

In this case, when the value thereof is caused to decrease from the present 100 (nA) to 10 (nA) with attention focused on the DC component, crossing the boundary occurs at point "d," which indicates falling into the region where measurement of the arterial oxygen saturation is impossible at 10 (nA).

As described above, when control is executed with attention focused only on the DC component, there are some cases where measurement of the arterial oxygen saturation is impossible even though the DC component is the same 100 (nA) when the DC component is caused to decrease to 10 (nA), depending on a status of a patient.

In order to avoid the problem, the LED driving current must be supplied such that the DC component is consistently 1,000 (nA) or higher so as to enable detection of the pulse wave at all times independent of the status of a patient (i.e., the AC component).

As mentioned above, the control that focuses attention solely on the DC component enables reduction of the LED driving current from the point "a" to the point "b." In spite of this fact, an LED driving current of 1,000 (nA) or higher is achieved at all times. Hence, difficulty is encountered in substantially saving power.

SUMMARY OF THE INVENTION

It is therefore an object of the invention to provide an apparatus for determining concentrations of light absorbing substances in blood, which enables substantial reduction in power consumption without causing a decrease in measurement accuracy.

In order to achieve the above object, according to the invention, there is provided an apparatus for determining a concentration of a light absorbing substance in blood, comprising;

a plurality of photo emitters, adapted to emit light beams having different wavelengths toward a living tissue including a blood vessel;

a photo receiver, adapted to receive the light beams which have been transmitted through or reflected from the living tissue;

a driver, which inputs driving currents for causing the respective photo emitters to emit the light beams; and an optimizer, which obtains values of AC components of the light beams received by the photo receiver, and adjusts values of the driving currents such that the values of the AC components fall within a predetermined range.

Preferably, the optimizer comprises:

a first calculator, which further obtains values of DC components of the light beams received by the photo receiver, and calculates values of pulsation ratios which are ratios of the values of the AC components to the values of the DC components;

a second calculator, which calculates, based on the values of the DC components and the values of the pulsation ratios, optimized current values corresponding to minimum expected values of the AC components which are inherent in the apparatus; and a controller, which causes the values of the driving currents to coincide with the optimized current values.

In other words, by adding a function of controlling current values for driving the photo emitters such that an AC component value of light transmitted through a patient falls within a predetermined range, driving minimum current values optimal to an individual patient can be obtained in accordance with the condition of the patient. Accordingly, there can be realized an apparatus for determining concentrations of light absorbing substances in blood which enables substantial reduction in power consumption without causing decrease in measurement accuracy.

In addition, by virtue of attainment of the substantial reduction in power consumption, the apparatus for determining concentrations of light absorbing substances in blood can be made portable or embodied as a telemeter.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

Figure 1A:
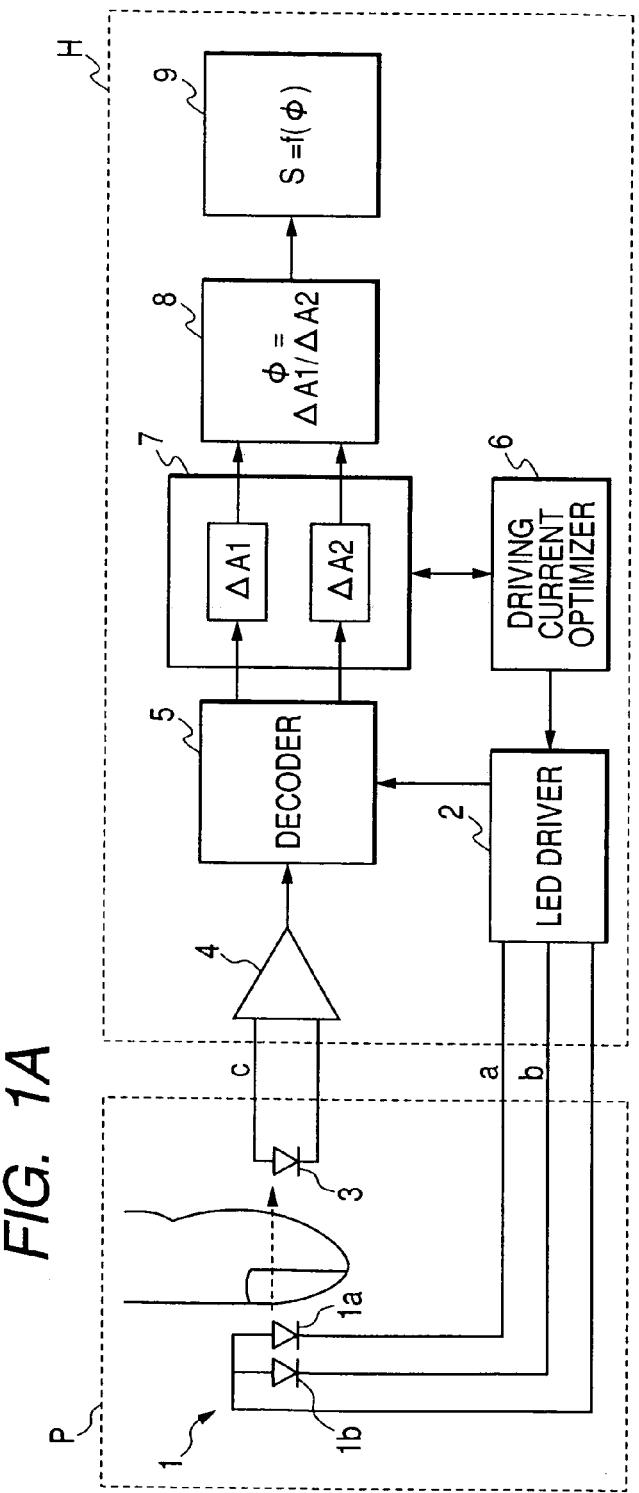
FIG. 1A is a block diagram showing a pulse oximeter according to one embodiment of the invention.
Figure 1B:
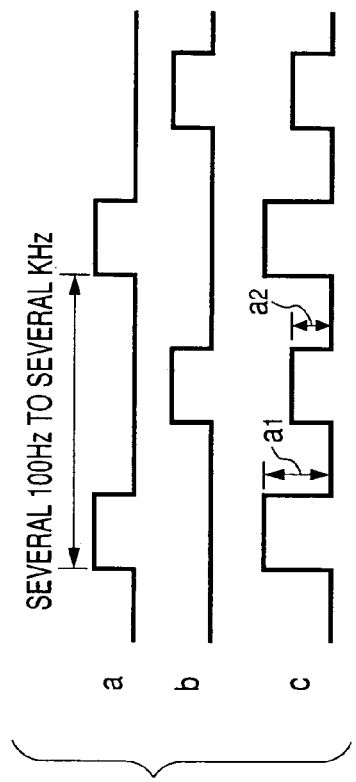
FIG. 1B is a time chart showing the timings of input and output signals of a probe in the pulse oximeter of FIG. 1A.
Figure 5A:
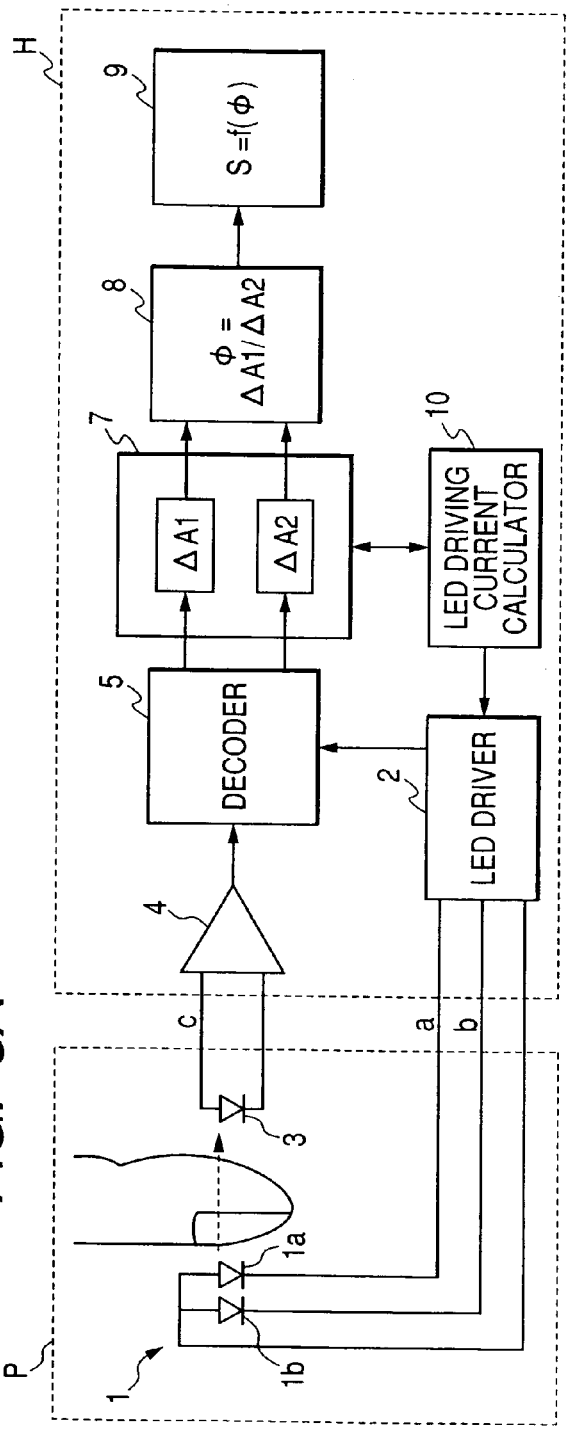
FIG. 5A is a block diagram showing a conventional pulse oximeter according to one embodiment of the invention.
Figure 5B:
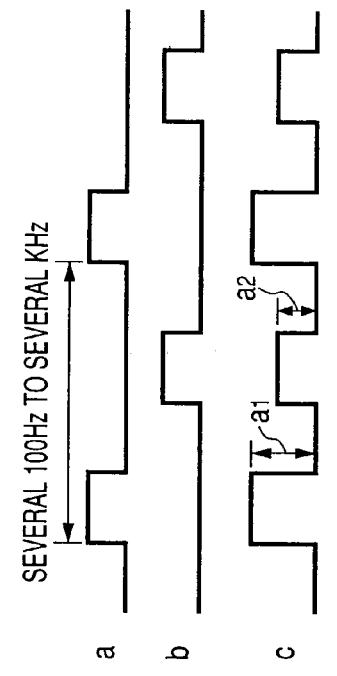
FIG. 5B is a time chart showing the timings of input and output signals of a probe in the pulse oximeter of FIG. 5A.

Embodiments of the invention will be described below in detail with reference to the accompanying drawings. In FIGS. 1A and 1B, a pulse oximeter is taken as an example of an apparatus for determining concentrations of light absorbing substances in blood of the invention. The same component as those in the conventional pulse oximeter shown in FIG. 5 will be designated by the same reference numeral, and repetitive explanations for those will be omitted.

In this embodiment, in order to attain substantial reduction in power consumption without causing a decrease in measurement accuracy, the Driving current optimizer 6 is provided. The Driving current optimizer 6 receives data on a DC component of transmitted light, an AC component of the transmitted light, and pulsation ratio output from the pulsation ratio detector 7; and controls current supplied from the LED driver 2 to the LED section 1. Accordingly, the AC component of the transmitted light reaches a predetermined value.

In the LED driving current control which focuses attention on the AC component, a minimum value of the AC component with which the arterial oxygen saturation (SpO2) can be measured is determined depending on characteristics of a pulse oximeter, and the like. In the invention, control is executed such that an amount of light emitted from the LEDs reaches the value of the thus-determined AC component.

Figure 4:
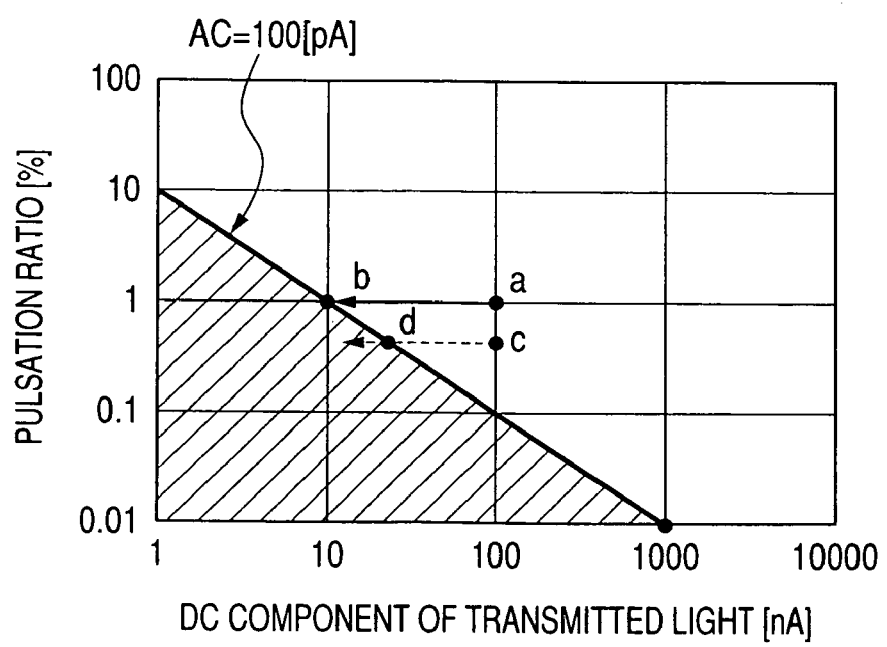
FIG. 4 is a diagram for explaining the possibility of determination of an oxygen saturation.

As a more specific example, in a case of the LED driving current control which focuses attention on the AC component, there is executed control such that, in a case of the point "a" in FIG. 4, the LED driving current section 1 is caused to decrease until the AC component reaches 100 (pA), whereby the state moves from the point "a" to the point "b."

The point "b" is a point associated with a lower limit of a region where measurement of the arterial oxygen saturation (SpO2) is possible and at which both the AC component and the DC component are minimum but sufficient values. Accordingly, an amount of light emitted from the LED section 1 (power consumption) can be suppressed to its minimum while measurement accuracy is maintained at a certain level or higher.

Furthermore, in a case of the point "c" in FIG. 4, there is executed control such that the LED driving current section 1 is caused to decrease until the AC component reaches 100 (pA), thereby moving from the point "c" to the point "d." The point "d" is also a point associated with a lower limit of the region where calculation of the arterial oxygen saturation (SpO2) is possible and at which both the AC component and the DC component are minimum but sufficient values. Accordingly, an amount of light emitted from the LED section 1 (power consumption) can be suppressed to its minimum while measurement accuracy is maintained at a certain level or higher.

As described above, as a result of control focusing attention on the AC component being performed, control becomes feasible even in a region where control cannot be effected by the control focusing attention solely on a DC component. Therefore, substantial reduction in power consumption can be attained.

Figure 2:
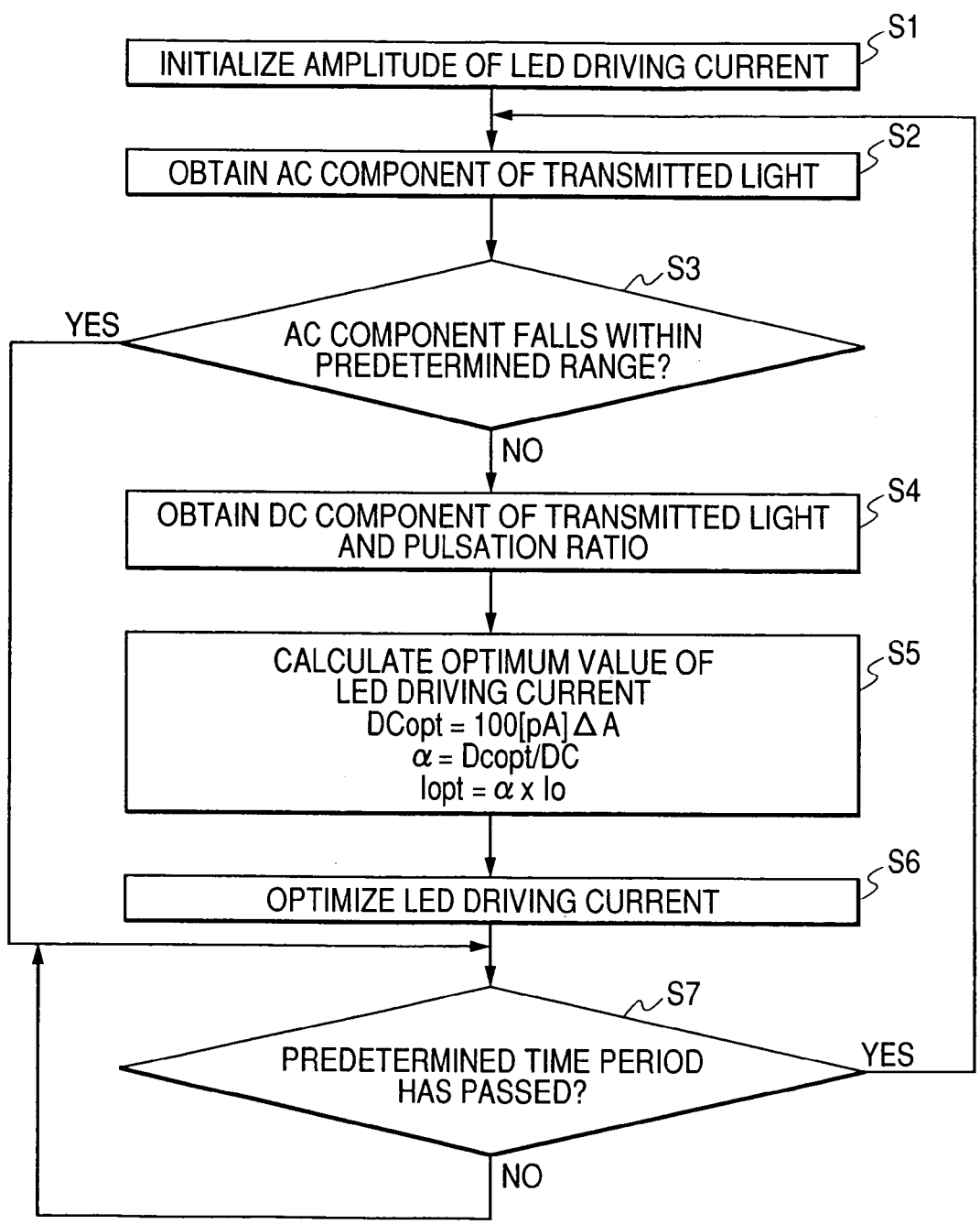
FIG. 2 is a flow chart showing processings for controlling an LED driving current in the pulse oximeter of FIG. 1A.

Next, a flow of control of the LED driving current which is executed by the Driving current optimizer 6, and in which attention is focused on the AC component will be described by reference to the flowchart shown in FIG. 2.

As preprocessing before usage of the pulse oximeter shown in FIG. 1, an LED driving current, which is such a current that, when the current is supplied to a majority of patients, an AC component of the transmitted light obtained therefrom is sufficient for measurement, is set as an initial value (lo). Thereafter, the probe P is attached to a finger of a patient, and the current (lo) is supplied thereto (step S1). Then, an AC component of the transmitted light (AC) is obtained (step S2).

Determination is made as to whether or not the AC component of the transmitted light (AC) obtained in step S2 falls within a predetermined range (100 pA$\leq$AC$\leq$ a predetermined value AC1) whose lower limit is a predetermined value (100 pA in case of FIG. 4) (step S3). The predetermined value AC1 is set to an optimum value in consideration of an allowable range for, e.g., response in control system or reduction of power consumption.

If the result of determination in step S3 is YES, the routine proceeds to step S7; and a determination is made as to whether or not a predetermined time T (sec) has passed after YES has been determined in step S3; that is, after the AC component of the transmitted light has been determined to fall within the predetermined range (step S7).

If the result of determination in step S3 is NO, the DC component of the transmitted light (DC) and the pulsation ratio ($\Delta$A) are obtained (step S4). Then, an optimum value (lopt) of the LED driving current is obtained in accordance with the following equations (step 85).

DCopt=100 (*pA*)/$\Delta A$;

$\alpha$=DCopt/DC; and lopt=$\alpha$·lo where, DCopt is an optimum value of the DC component of the transmitted light; and $\alpha$ is a change ratio of the LED current.

In step S6, the LED driver 2 controls an amplitude of the LED driving current such that an optimized LED driving current (lopt) is supplied to the LED section 1 (optimization). Then, determination is made as to whether or not the predetermined time T (see) has passed after the optimization (step S7). If the result of determination in step S7 is NO, processing (determination) in step S7 is repeated. If the result of determination in step S7 is YES, the routine returns to step S2.

As described above, the LED driving current is periodically subjected to optimization control so that the AC component of the transmitted light falls within a predetermined range. Therefore, power consumption of the LED section 1 can be suppressed to its minimum while measurement accuracy is securely maintained at a certain level or higher.

Figure 3:
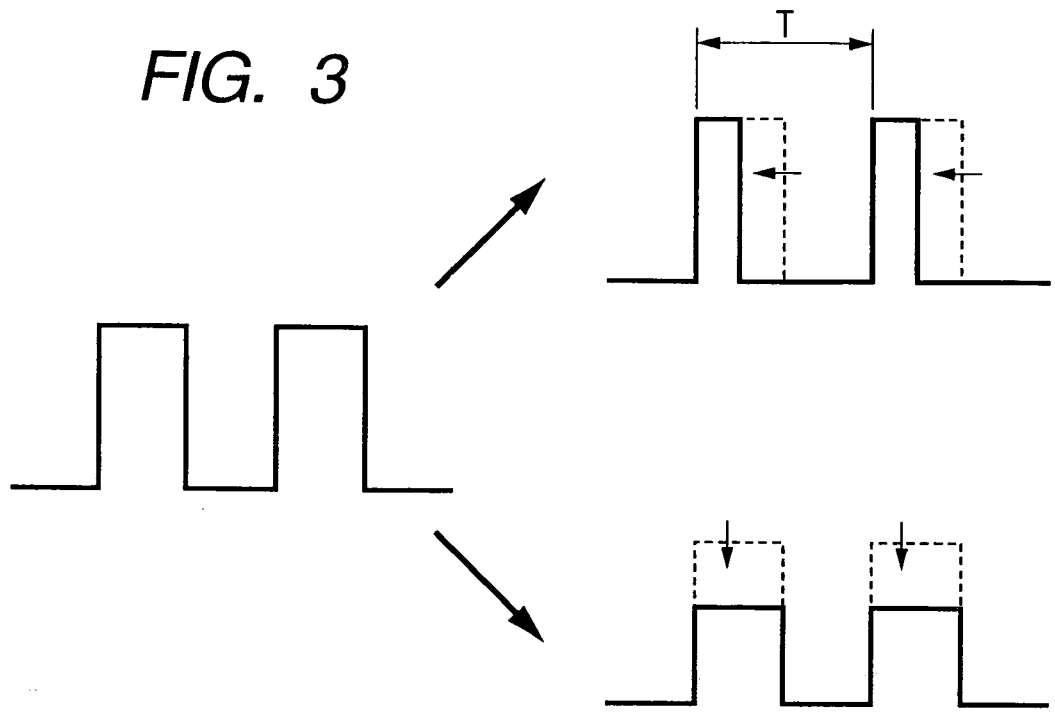
FIG. 3 is a diagram for explaining how to control the mean current value of the LED driving current.

The control method for reducing power consumption according to the invention is fulfilled as a control mode for controlling mean current of the drive current supplied to the LED section, by decreasing an amplitude of current pulse or narrowing a width of current pulse in a single period as shown in FIG. 3.

The foregoing description has been made while a pulse oximeter is taken as an example; however, the present invention is not limited thereto. The invention can be applied to other devices for determining concentrations of light absorbing substances in blood which utilize the principle of pulse photometry, such as an apparatus for determining hemoglobin concentration, an apparatus for determining dye concentration, an apparatus for determining bilirubin concentration, or an apparatus for determining blood glucose level.

What is claimed is:

1. An apparatus for determining a concentration of a light absorbing substance in blood, comprising:

a plurality of photo emitters, adapted to emit light beams having different wavelengths toward a living tissue including a blood vessel;

a photo receiver, adapted to receive the light beams which have been transmitted through or reflected from the living tissue;

a driver, which inputs driving currents for causing the respective photo emitters to emit the light beams; and an optimizer, which obtains values of AC components of the light beams received by the photo receiver, and adjusts values of the driving currents such that the values of the AC components fall within a predetermined range.

2. The apparatus as set forth in claim 1, wherein the optimizer comprises:

a first calculator, which further obtains values of DC components of the light beans received by the photo receiver, and calculates values of pulsation ratios which are ratios of the values of the AC components to the values of the DC components;

a second calculator, which calculates, based on the values of the DC components and the values of the pulsation ratios, optimized current values corresponding to minimum expected values of the AC components which are inherent in the apparatus; and a controller, which causes the values of the driving currents to coincide with the optimized current values.

* * * * *